(12) United States Patent
Hughes et al.

(10) Patent No.: US 9,222,927 B2
(45) Date of Patent: Dec. 29, 2015

(54) DISSOLUTION TEST EQUIPMENT

(75) Inventors: Lyn Hughes, Harleysville, PA (US);
Donald Frederick Wright, Richboro, PA (US)

(73) Assignee: Rohm and Haas Company, Philadelphia, PA (US)

( * ) Notice: Subject to any disclaimer, the term of this patent is extended or adjusted under 35 U.S.C. 154(b) by 795 days.

(21) Appl. No.: 13/196,184

(22) Filed: Aug. 2, 2011

(65) Prior Publication Data
US 2012/0034704 A1 Feb. 9, 2012

Related U.S. Application Data

(60) Provisional application No. 61/400,889, filed on Aug. 4, 2010.

(51) Int. Cl.
*G01N 33/15* (2006.01)
*G01N 1/18* (2006.01)
*B01F 13/10* (2006.01)
*G01N 13/00* (2006.01)
*G01N 35/00* (2006.01)

(52) U.S. Cl.
CPC ............. *G01N 33/15* (2013.01); *B01F 13/1013* (2013.01); *G01N 1/18* (2013.01); *G01N 2013/006* (2013.01); *G01N 2035/00198* (2013.01); *Y10T 436/255* (2015.01)

(58) Field of Classification Search
CPC .... G01N 1/18; B01F 13/1013; B01F 1/10133
USPC ........................................................... 422/62
See application file for complete search history.

(56) References Cited

U.S. PATENT DOCUMENTS

| | | | |
|---|---|---|---|
| 4,279,860 A * | 7/1981 | Smolen | ........................... 422/63 |
| 5,412,979 A * | 5/1995 | Fassihi | ......................... 73/53.01 |
| 5,807,115 A | 9/1998 | Hu | |
| 6,799,123 B2 | 9/2004 | Hughes | |
| 2003/0088369 A1* | 5/2003 | Hughes | ........................... 702/25 |
| 2005/0166688 A1 | 8/2005 | Tian et al. | |
| 2007/0092404 A1 | 4/2007 | Hughes | |
| 2007/0160497 A1 | 7/2007 | Hughes et al. | |

FOREIGN PATENT DOCUMENTS

JP   2004-233332 A   8/2004

OTHER PUBLICATIONS

Ashok C. Shah, Craig B. Peot, and John F. Ochs; "Design and Evaluation of a Rotating Filter-Stationary Basket In Vitro Dissolution Test Apparatus I: Fixed Fluid Volume System" vol. 62, No. 4, Apr. 1973 pp. 671-677.*

(Continued)

*Primary Examiner* — Christopher A Hixson
*Assistant Examiner* — Emily Berkeley
(74) *Attorney, Agent, or Firm* — Carl P. Hemenway; Marcella M. Bodner

(57) ABSTRACT

Apparatus and method for dissolution testing of active substances in various dosage forms is provided. The apparatus has filtration cells equipped and configured to simulate bodily functions, operate continuously and facilitate testing various types of dosage forms including, but not limited to, tablets, capsules and those having non-disintegrating substrates.

7 Claims, 2 Drawing Sheets

(56) References Cited

OTHER PUBLICATIONS

Ngoc, et al., "Evaluation of a Continuous Fluid Exchange System in the USP Basket-Stirrer Dissolution Test Assembly." J. Pharm. Belg., vol. 31, No. 6, pp. 589-598 (1976).

Ngoc, et al., "Evaluation of a Continuous Fluid Exchange System in the USP Basket-Stirrer Dissolution Test Assembly.", J. Pharm. Belg., vol. 32, No. 1, 67-75 (1977).

Takenaka, et al., "Preparation of Enteric-Coated Microcapsules for Tableting by Spray-Drying Technique and In Vitro Simulation of Drug Release from the Tablet in GI Tract", J. Pharm. Sci., vol. 69 pp. 1388 (1980).

Pernarowski, et al., "Continuous Flow Apparatus for the Determination of the Dissolution Characteristics of Tablets and Capsules", J. Pharm. Sci., vol. 57, pp. 1419-1421(1968).

\* cited by examiner

DISSOLUTION TEST EQUIPMENT

This application claims the benefit of priority under 35 U.S.C. §119(e) of U.S. Provisional Patent Application No. 61/400,889 filed on Aug. 4, 2010.

FIELD OF THE INVENTION

The present invention relates to an apparatus and method for testing the dissolution rate of active substances in various dosage forms. The apparatus includes filtration cells which are designed to simulate bodily functions, operate continuously and facilitate testing various types of dosage forms including, but not limited to, tablets, capsules and those having non-disintegrating substrates.

BACKGROUND

The rate at which pharmaceutically active compounds dissolve in gastrointestinal fluids is of crucial importance in the design and use of orally administered medications. The active compound must be dissolved before it can be absorbed by the body. The rate at which the active substance enters into solution is know in the art as the dissolution rate, and the determination of the dissolution rate in vitro is known as dissolution testing.

The concept of using in vitro data to predict or model in vivo behavior, referred to as in vitro—in vivo correlation, or IVIVC, is of great interest to the pharmaceutical arts. Test methods with good IVIVC are much more capable of detecting problems with existing formulations and in the development of new formulations. Systems which correlate closely with the dissolution and absorption data obtained in vivo can be used in developing dosage forms as well as in the production, scale-up, determination of lot-to-lot variability, testing of new dosage strengths, testing of minor formulation changes, testing after changes in the site of manufacture and for determining bio-equivalence.

Various methods and devices for dissolution measurement are well known and described in the art.

The US Food and Drug Administration (US FDA) has issued guidelines on the levels of correlation that are more or less desirable in in vitro testing (Guidance for Industry, Extended Release Oral Dosage Forms: Application of In vitro/In vivo Correlations, September 1997). A Level A correlation is one that predicts the entire in vivo time course from the in vitro data. A Level B correlation is one that uses statistical moment analysis. The mean dissolution time is compared either to the mean residence time or to the mean in vivo dissolution time. A Level C correlation establishes a single point relationship between a dissolution parameter and a pharmacokinetic parameter. Level B and Level C correlations do not reflect the complete shape of the plasma concentration-time curve. A Multiple Level C correlation relates in vitro data at several time points to several pharmacokinetic parameters. It is generally considered that if a multiple level C is possible, then Level A correlation should also be possible. Rank order correlations are those where only a qualitative relationship exists between in vitro and in vivo. A Level A correlation is considered to be the most informative and is recommended by the USFDA wherever possible. Multiple Level C correlations can be as useful as Level A, but a Level A is preferred. Having a high level of correlation, eg Level A, can reduce the amount of in vivo testing necessary for new formulations and can therefore be very valuable to pharmaceutical companies.

The conditions that affect dissolution in the gastro-intestinal system are known to vary with position within the gastro-intestinal system. These variations can affect the rate of dissolution of active substances. There have been attempts to simulate these changes in in vitro testing. The main focus has been on the very large pH change between the stomach and upper GI. This change is large enough to have a very serious effect on the solubility of some active substances. For example, diclofenac sodium is essentially insoluble at the low pH of the stomach, but is soluble at the near neutral conditions of the upper GI. In the current art this change of pH has been addressed in two ways. The first has been to change the fluid used in the dissolution test, for example start with gastric fluid and then change to intestinal fluid. The second has been to change the pH gradually by addition of a higher pH solution. Neither of these methods adequately simulates the pH change in vivo because in both methods all the formulation experiences the pH change at the same time, whereas in vivo the pH change is controlled by gastric emptying which causes a gradual transfer of the disintegrated formulation so that different portions of the formulation experience the pH changes at different times. In U.S. Pat. No. 5,807,115, Hu states that it is difficult to move an already disintegrated solid sample. Hu uses this conclusion to justify the gradual change of pH described above.

A method that has been used to solve the problem associated with the USP fixed volume and flow-through methods has been the continuous flow cell in which either the contents of the cell is stirred, or a part of the effluent is recycled to the cell. This allows equilibrium effects to be evaluated.

The equipment described by Huynh-Ngoc and Sirois (J. Pharm Belg, 1976, 31, 589-598; ibid 1977, 32, 67-75) is a continuous flow apparatus. The equipment was designed to facilitate replacement of gastric fluid with intestinal fluid to simulate the transit of the test material through the gastrointestinal system. The authors establish only a rank order IVIVC. Takenaka, Kawashima and Lin (J. Pharm Sci, 69, 1388-1392, 1980) describe an apparatus similar in form to that of Huynh-Ngoc and Sirois. The authors made no connection between their data and in vivo performance, although it is clear to one skilled in the art that the limitations will be the same as those for the Huynh-Ngoc and Sirois equipment. Pernarowski, Woo, and Searl (J. Pharm Sci, 57, 1419-1421, 1968) also report the use of a continuous flow method. The authors do make comparison of their results with in vivo performance but it is only a rank order correlation. In all of the flow-through systems described above only one cell is used per test. There are multiple cell systems available commercially, but these have multiple cells in parallel so that each cell is independent of the other and hence they are a plurality of single cell systems. Dissolution testing provides a better understanding of the amount of a pharmaceutically active compound available at a particular absorption site at various times. In addition, establishing a relationship between dosage form and availability of a pharmaceutically active compound at certain absorption sites and systemic blood levels of such active compound aids in the development of specialized delivery techniques.

In U.S. Patent Application Publication Nos. 2007/0092404 and 2007/0160497, improved continuous flow dissolution test apparati, similar to that described in U.S. Pat. No. 6,799,123 are disclosed, along with methods for using them. In particular, U.S. Patent Application Publication No. 2007/0092404 describes using a filter support in the chamber of the second cell, positioned between the filter and the base (interior bottom surface) of the chamber to prevent distortion of the filter as it collects undissolved solids thereon.

On the other hand, U.S. Patent Application Publication No. 2007/0160497 discloses a sample holder device which operates with the sample addition port of the lid of a cell to enable addition and removal of a dosage form to the chamber within the same cell, during continuous operation of the multiple flow-through cell dissolution test system, without having to stop the flow of media or expose the contents of the chamber to the ambient environment.

There is also need for an in vitro test that can be used with different dosage forms of the same active ingredient that gives Level A IVIVC for other dosage forms without the need for different test conditions for each dosage form.

BRIEF DESCRIPTION OF THE DRAWINGS

A more complete understanding of the present invention will be gained from the embodiments discussed hereinafter and with reference to the accompanying drawings, wherein.

STATEMENT OF THE INVENTION

Figure 1:
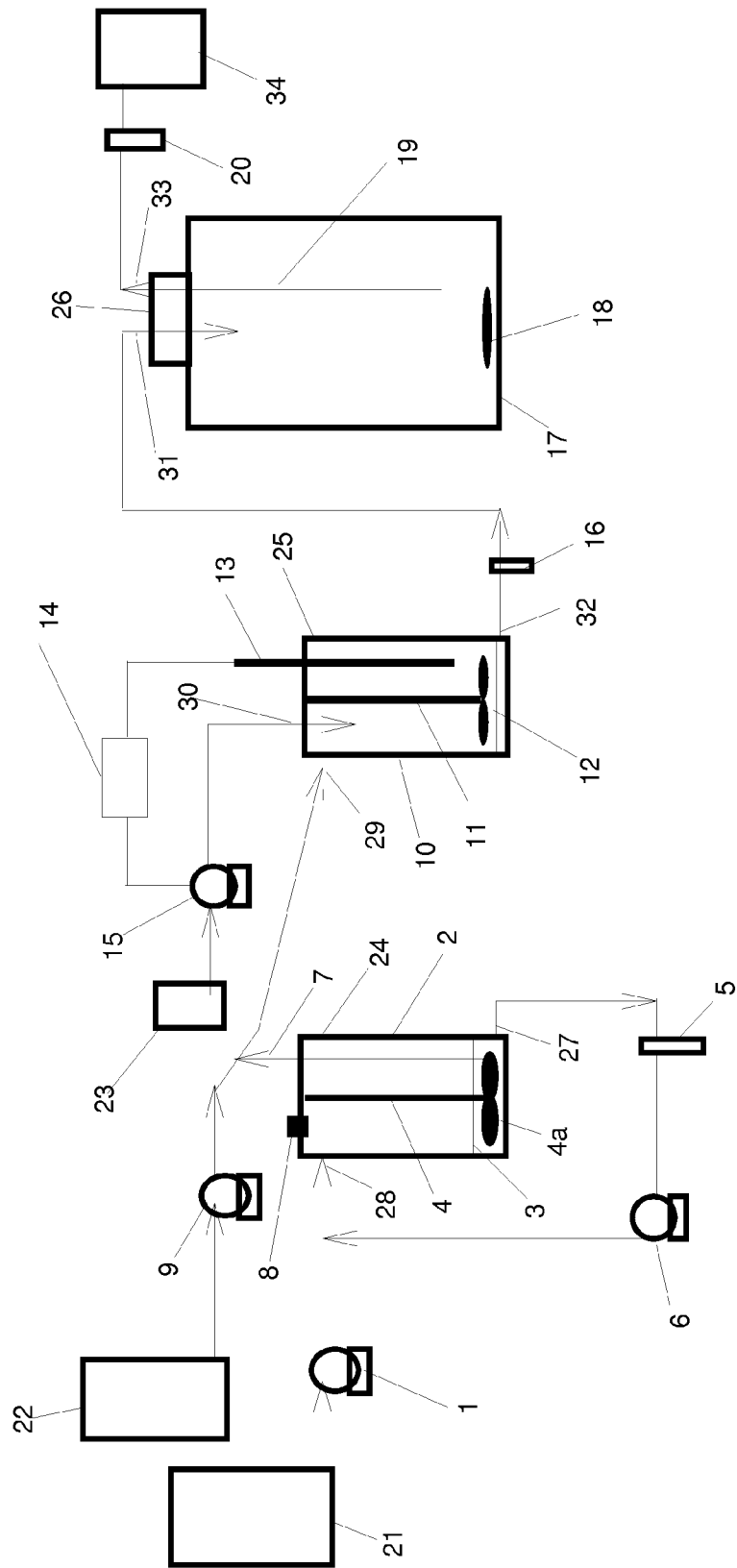
FIG. 1 is a schematic representation of one embodiment of the invention comprising three cells.

The present invention relates to an apparatus for conducting dissolution tests comprising:
a) a first chamber comprising a base and a shelf screen and being capable of transferring solid particles to said second chamber;
b) a second chamber connected in series to said first chamber and being capable of retaining solids;
c) at least one supply of media that can be continuously passed into one or more of said chambers;
d) a means of analyzing effluent from said chambers for substances of interest in the tests;
e) a means of controlling temperature of medium in each of said chambers;
wherein each of said chambers has a means of adding a sample and means for mixing the sample and medium; and wherein said mixing means of said first chamber is proximate to said base and said shelf screen is held by a retainer and positioned above said mixing means, on an opposite side of said mixing means from said base.

The sample may be a dosage form comprising one or more active ingredients, one or more inactive ingredients and one or more substrate material. Furthermore, the dosage form may be a non-disintegrating dosage form wherein at least a portion of said substrate does not dissolve in said medium.

The shelf screen should be a mesh screen compatible with said medium and having a have a mesh size of from 200 mesh to 10 mesh.

In one embodiment, the apparatus further comprises a third chamber connected in series to said second chamber. In such an embodiment, the apparatus may further comprise: at least one supply of media that can be continuously passed into the third chamber; means for mixing media in the third chamber; a means of analyzing effluent from the third chamber for substances of interest.

The present invention also provides a dissolution test method using the above-described apparatus, comprising the steps of:
a) passing one or more media through at least the first and second chambers;
b) adding the test sample to the first chamber;
c) passing medium through each of the chambers such that any undissolved portion of the sample is transferred from the first chamber into the second chamber;
d) passing medium through the chambers such that any undissolved portion of the sample remains in the second chamber;
e) maintaining the temperature of the media in the chambers at the desired temperature for the duration of the test; and
f) analyzing effluent from each of the chambers to determine the concentration of substance dissolved from the test sample.

DETAILED DESCRIPTION OF THE INVENTION

The present invention relates to an apparatus for conducting dissolution tests wherein the sample (or dosage form) need not be completely disintegrated or dissolved in the filtration cell for the test to proceed continuously and accurately. The apparatus comprises a) at least a first chamber (filtration cell) comprising a base and a shelf screen and being capable of transferring solid particles to said second chamber; b) a second chamber (filtration cell) connected in series to said first chamber and being capable of retaining solids; c) at least one supply of media that can be continuously passed into one or more of said chambers; d) a means of analyzing effluent from said chambers for substances of interest in the tests; and e) a means of controlling temperature of medium in each of said chambers. Each of the chambers/filtration cells has a means of adding a sample and means for mixing the sample and medium (i.e., an agitator). Furthermore, in accordance with the present invention, and as described in further detail hereinafter, the mixing means of the first chamber is proximate to its base and the shelf screen is held by a retainer and positioned above the mixing means, on the opposite side of the mixing means from the base.

The following terms have the following meanings herein:

The terms "medium", "media", or "release medium" as used herein, means the liquid medium into which the active substance is being released. Examples of release media can be water, simulated intestinal fluid, simulated gastric fluid, simulated saliva, or the authentic physiological versions of these fluids, water, and various buffer solutions.

The term "residence time" as used herein, is a well known engineering concept applied to continuous flow systems, and is calculated by mathematically dividing the volume of liquid in a vessel by the flow rate into an out of the vessel such that the volume of liquid remains constant. For example, a flow rate of 5 ml/min into and out of a vessel containing 10 ml of liquid has a residence time of 2 minutes.

The term "dosage form," "sample," "composition," "agent," "compound", or "substance" as used herein, means a chemical, a material, a composition, a blend, or a mixture of materials or components that will at least partially dissolve within a release medium to release an active agent. The terms characteristics, parameters, and specifications may be used interchangeably herein and are intended to refer to some property, ingredient, quantity, quality, etc. of a composition or dosage form.

The term "$C_{max}$" as used herein, means the maximum concentration observed in the blood plasma concentration vs time curve for in vivo data, or the cell effluent concentration vs time curve for in vitro data.

The term "$t_{max}$" as used herein, means the time taken to reach $C_{max}$ after the administration of the drug, either in vivo, or in vitro.

The term "gastric chamber" as used herein, refers to the first of three chambers or cells of the current invention, the design and function of which is described hereinbelow.

The term "intestinal chamber" as used herein, refers to the second of three chambers or cells of the current invention, the design and function of which is described hereinbelow.

The term "circulatory chamber" as used herein, refers to the third of three chambers or cells of the current invention, the design and function of which is described hereinbelow.

The terms "release profile" and "dissolution profile" as used herein, mean the change in concentration with time of the substance being tested.

FIG. 1 schematically illustrates one embodiment of the dissolution apparatus of the present invention. A reservoir (21), a pump (1), and a filtration cell (2) are connected such that the liquid contents of the reservoir (21) are transferred into the filtration cell (2) via the pump (1). The filtration cell (2) is equipped with a tight fitting lid (24), an inlet (28), a shelf screen (3), an agitator (4), an outlet (27) positioned to allow removal of filtered liquid, and a content removal assembly (7). The outlet (27) is connected to a flow-thru uv cell (5) and a pump (6), such that the filtrate is pumped through the uv cell (5) and returned to the inlet of the filtration cell (2). The filtration cell (2) may also have a sample addition port (8) for providing a dosage form containing one or more active ingredients to the filtration cell (2).

Figure 2:
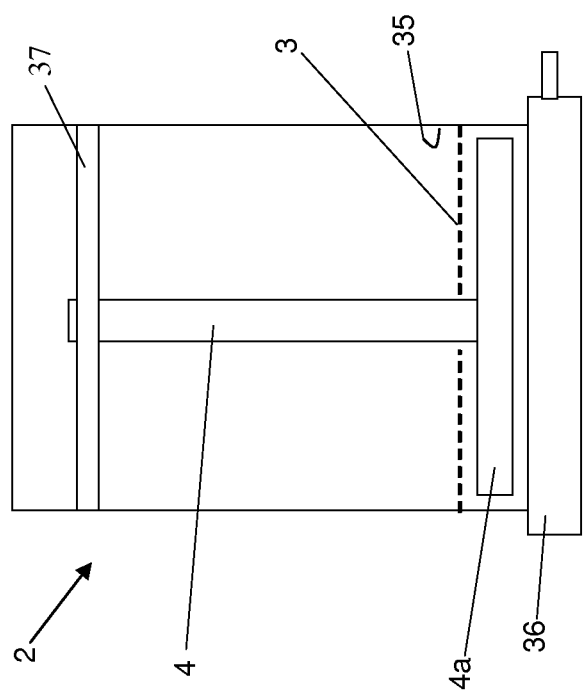
FIG. 2 is a schematic elevational side view of a filtration cell having an agitator and a shelf screen.
Figure 3:
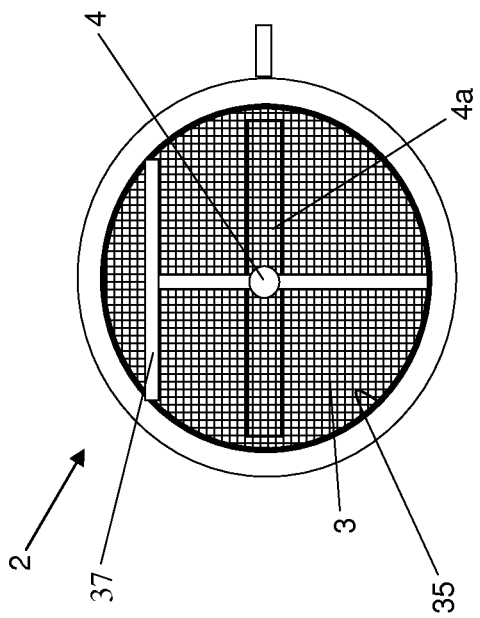
FIG. 3 is a schematic top plan view of the filtration cell of FIG. 2.

With reference to FIGS. 2 and 3, in accordance with the present invention, the agitator (4) is held in the cell (2) by an agitator support (37) and includes a rotating portion (4a) positioned proximate the base (36) of the cell (2). The rotating portion (4a) rotates in a plane parallel to the base (36). The agitator (4) mixes the contents of the cell (2), thereby facilitating disintegration and dissolution of the various components (i.e., active ingredients, substrate material, inactive ingredients, etc.) of the sample (not shown).

It has been found that as the components of the sample disintegrate and dissolve, larger solid particles sometimes form and drift to the base (36) of the cell (2). Since the distance between the rotating portion (4a) of the agitator (4) and the base (36) or surface of the inner wall (35) of the cell (2) is small, such large solid particles would sometimes be large enough to interfere with movement and operation of the agitator (4). This, in turn, hindered proper mixing of the cell contents and required the dissolution test process to be interrupted, and even halted and started all over again with a new sample and fresh fluids. Of course, such situations are wasteful of resources and time. In similar fashion, addition of tablets or capsules to the cell (2) without the use of a retaining basket or coil often result in said tablet or capsule interfering with and stopping the agitator.

To address the foregoing disruptions caused by whole dosage units and solid particles from the sample (not shown) hindering operation of the agitator (4), a shelf screen (3) which is sized and shaped to fill the entire cross-section of the filtration cell (2) is used as can be seen in FIG. 3. The shelf screen (3) is suspended in the filtration cell (2), above the rotating portion (4a) of the agitator (4), to catch and retain solids that may form during disintegration and dissolution of the sample. In the embodiment shown in FIGS. 2 and 3, the circumferential edge of the shelf screen (3) is tightly fitted in a groove (not shown per se) formed on the interior surface of the wall (35) of the cell (2) such that the shelf screen (3) is firmly held in place without further holding devices. When the shelf screen (3) is used with an agitator (4) of the design shown in FIG. 2 said screen has a hole in its center to accommodate the shaft of agitator (4). The clearance between the shelf screen (3) and said agitator shaft is as small as possible without affecting the operation of the agitator (4). It is believed that persons of ordinary skill can easily devise other retaining methods to suspend the shelf screen (3) in the filtration cell (2) above the rotating portion (4a) of the agitator (4). For example, inwardly projecting tabs (not shown) may be affixed to the inner wall of the cell (2), or they may be integrally formed with the cell wall. Also, a tight fitting O-ring can be installed in a groove (not shown) of the wall of the cell (2) with a portion thereof extending into the cell for supporting the circumferential edge of a screen shelf thereon.

Moreover, sometimes the sample to be tested has one or more active ingredients carried on, or embedded in, a substrate which does not disintegrate, or which does not disintegrate completely. Such samples are said to be "non-disintegrating dosage forms" and are common. Non-disintegrating dosage forms will always produce large solid particles which would interfere with operation of the agitator (4) if allowed to sink to the base (36) of the filtration cell (2). Thus, filtration cells having a shelf screen (3) are particularly well-suited for conducting dissolution testing of non-disintegrating dosage forms.

Shelf screens (3) useful in the practice of this invention may, for example, be any of the commercially available mesh screens that are compatible with preventing large solid particles interfering with the agitator while allowing free passage of release media such that the mixing provided by the agitator (4) is still effective in the portion of the cell (2) above the shelf screen (3). Thus, suitable screens have a mesh size of from 200 mesh to 10 mesh. For example, without limitation, screens having a mesh size of from 50 to 16 mesh have been found to be particularly useful.

The material of construction of the screens used in the screen shelf can be of any material compatible with the release medium but must have sufficient rigidity that it does not sag or move during operation. A particularly suitable material of construction of the screens is stainless steel, being both compatible with the typical release media and of sufficient rigidity. As will be clear to persons having ordinary skill in the relevant art, less rigid screens can be used when combined with a suitable support.

Shelf screens (3) useful in the practice of this invention may, for example, be any of the commercially available mesh screens that are compatible with preventing large solid particles interfering with the agitator, while allowing free passage of release media and dissolved sample, such that the mixing provided by the agitator (4) is still effective in the portion of the cell (2) above the shelf screen (3).

The content removal assembly (7) is configured to remove liquid and small sized particle solids from the filtration cell (2) for transport, along with liquid from a reservoir (22) to a second filtration cell (10). The reservoir (22) is connected to a pump (9) such that the liquid from the reservoir (22) is fed through the content removal assembly (7), to an inlet (29) of the second filtration cell (10). The filtration cell (10) is equipped with a tight fitting lid (25), a pH sensor (13), a stirrer (11), two inlets (29 and 30), and an outlet positioned to allow removal of filtered liquid (32). The second filtration cell (10) may or may not also have a screen shelf (not shown) which may be configured and operate similarly to the shelf screen (3) as described above in the first filtration cell (2). If the second filtration cell (10) does have a shelf screen, the filtration membrane (12) positioned underneath the rotating portion (4a) of the agitator (4), as shown schematically in FIG. 1 is still required.

Another reservoir (23) is connected to a pump (15) and to one of the inlets (30) of the filtration cell (10), such that liquid from the reservoir (23) is transferred into the filtration cell (10). The outlet (32) is connected to a flow-thru uv cell (16). The outlet of the uv cell (16) is connected to the inlet (31) of a third cell (17). The pH sensor (13) is electrically connected to a pH controller (14). The power supply to pump (15) is connected to the output relay of the pH controller (14) such that the pump (15) is turned on when the pH as measured by the pH sensor (13) is below a target value, and is turned off when said pH is above a target value.

The third cell (17) is equipped with a tight fitting lid (26), a stirrer (18), a dip-tube (19), and an outlet (33). The outlet (33) is connected to the inlet of a flow-thru uv cell (20). The outlet from the uv cell (20) is directed to waste or any suitable reservoir (34). A means for temperature control may also be provided to manage the temperature of the third cell (17) and it contents, but this is not necessary.

In this embodiment, the filtration cell (2) and immediately associated equipment represents the gastric chamber, or stomach, of a human; the second filtration cell (10) and immediately associated equipment represents the intestinal tract of a human; and the third cell (17) and immediately associated equipment represents the circulatory chamber, or blood, of a human.

Each of the flow-thru uv cells (5, 16, and 20) is placed in a suitable uv spectrophotometer capable of measuring the absorbance of the cell contents at the desired wavelength.

When control of the temperature is required any or all of the three cells can be placed in a suitable heated enclosure, for example an oven or a heating bath, which are very well known in the industry.

In one embodiment, reservoir (21) is filled with simulated gastric fluid, reservoir (22) is filled with simulated intestinal fluid, and reservoir (23) is filled with 0.8M aqueous sodium hydroxide solution. To start a test, the pumps are operated to fill each of the chambers to the desired volumes, and then run for sufficient time to establish that the flow rate from each pump is as desired and the pH of cell (10) is maintained within the target range. The uv cells are checked to make sure that they contain no air bubbles.

In one embodiment the sample addition port (8) of the filtration cell (2) is a hole with a rubber stopper (not shown per se). For said embodiment the pumps are momentarily stopped, the stopper is removed, and the sample to be tested is added to the filtration cell (2). The stopper is immediately replaced and the pumps restarted.

In another embodiment, the sample addition port (8) may be an opening (not shown) in the lid (24) of the filtration cell (2), to which a device is sealingly attached which has a plunger and basket assembly or a plunger and coil assembly (not shown per se, but description in U.S. Patent Application Publication No. US2007/0160497). The basket of such a device is typically made of mesh and is sized and shaped to hold a sample while it is passed through the opening in the lid (24) and contacted with the liquid media in the cell (2) to dissolve. Non-disintegrating dosage forms often swell in size during contact with the liquid media and, therefore, delivery of non-disintegrating dosage forms using the aforesaid plunger and basket assembly is not practical. The coil of such a device is typically made of a length of steel wire arranged in a coil shape to hold a sample therein. While a coil may allow for swelling of the non-disintegrating dosage form, it is still possible for large solid particles to form during disintegrating of the sample and fall to the base of the cell where they interfere with operation of the rotating portion (4a) of the agitator (4). The shelf screen (3) of the present invention enables testing of non-disintegrating dosage forms in the filtration cell (2) by allowing placement of the dosage form (sample) on the shelf screen (3) during dissolution and, thereby, avoiding use of the plunger and basket, or plunger and coil, assembly and avoiding interference with operation of the rotating portion (4a) of the agitator (4) by undissolved or partially dissolved solids.

Exposure to the fluid in the gastric chamber causes the sample to be partially or completely disintegrated, and/or dispersed, and/or dissolved. The dissolved portion exits the gastric chamber via the content removal assembly (7) together with small particles of undissolved drug and/or excipient. Dissolved drug and/or dissolved excipient leaves the gastric chamber through the outlet (27). The liquid that exits though outlet (27) passes through the UV uv cell (5), where its UV absorbance at any desired wavelength is continuously monitored. Said liquid is continuously returned to the gastric chamber via the inlet (28). The material exiting the cell (2) via the content removal assembly (7) mixes with simulated intestinal fluid introduced from the reservoir (22) via the pump (9). This mixture then enters the intestinal chamber (10) via the inlet (29).

In the intestinal chamber (10), the incoming mixture is mixed with the contents of said chamber together with sodium hydroxide solution entering from pump (15). Because the sodium hydroxide flow is controlled by the pH of the contents of the cell (10) the result is that the acid present in the gastric fluid portion of the incoming mixture is neutralized. In the intestinal chamber (10), the undissolved portion of the incoming mixture has further opportunity to dissolve. Dissolved drug and/or dissolved excipient exits the intestinal chamber through the outlet (32). The filter membrane (12) prevents any undissolved drug and/or undissolved excipient from exiting said chamber. The liquid that exits though outlet (32) passes through the UV cell (16), where as UV absorbance at any desired wavelength is continuously monitored. The liquid exiting the UV cell (16) then enters the circulatory chamber via the inlet (31).

In the circulatory chamber the incoming medium is mixed with the medium already present in said chamber. The resulting mixture continuously exits the chamber via the dip-tube (19) and outlet (33). The liquid that exits though outlet (33) passes through the UV cell (20), where its UV absorbance at any desired wavelength is continuously monitored.

The data collected from the spectrophotometer can be used to calculate the instantaneous concentration of the active substance. The data can be used to characterize the release rate and the total amount of active substance released. Measuring the concentration of active substance in the effluent collected in the collection reservoir (34) permits the calculation of the total amount of active substance released.

While the embodiment of the invention described above and illustrated by the examples uses constant composition of release fluids within each test, it is clear that the compositions can be changed with time, for example, as taught by Waaler (J Pharm Sci, 82, 764-766, 1993), to simulate changing conditions within the body.

Test method variables are composition of release media, residence time in each of the three chambers, amount of the sample being tested, and temperature. By adjusting these variables it is possible to obtain a release rate profile that matches the plasma concentration profile observed in vivo. When practiced in the pharmaceutical industry the preferred temperature is 37° C., and the preferred composition of the release media are simulated gastric and simulated intestinal fluids, recommended compositions for both of which can be found in the most recent edition of the US Pharmacopeia. It is also clear to one skilled in the art that other additives, such as enzymes, bile acids, and surfactants, can be included where their need is demonstrated. The USFDA recommends that dissolution conditions be physiologically relevant. However, it is clear to one skilled in the art that the present invention can be adapted for conditions that are not physiologically relevant. Such conditions may be desirable when considerations such as speed of operation, unusual solubility, or non conventional dosage forms are taken into account. For example, applicant has determined in some cases that by proportionally reducing residence times, the time scale of the test can be considerably shortened without loss of useful information.

The invention can be used to test many different types of formulation. These can include, but are not restricted to, tablets, powders, pills, syrups, fast-melt tablets, hard capsules and soft capsules. The medium analysis device includes, but is not limited to, any detector known in the art that generates physical and/or chemical data of a pharmaceutical or active test agent, e.g., the use of a UV spectrophotometer as the method of analysis. In a preferred embodiment, the detector is capable of acquiring data characteristic of a particular agent by method selected from the group consisting of ultraviolet radiation, infrared radiation, nuclear magnetic resonance, Ramen spectroscopy, electrochemical, biosensors, refractometry, optical activity, and combinations thereof. Any in-line detector known in the art that is applicable to the active substance and release medium can be also be used. Preferably, the medium dissolution analysis device is a detector that has a sensor communicatively attached thereto. In the preferred embodiment, there is at least one medium dissolution analysis device per dissolution chamber. For example, for each sample to be analyzed there is a corresponding medium dissolution analysis device capable of continuously generating physical and/or chemical data characteristic of the agent to be analyzed.

The medium analysis device preferably includes a detector operatively associated with the dissolution medium for at least the time period required for the dosage form to release the maximum releasable quantity of therapeutically active agent and a data processor for continually processing the generated data for at least the time period required for the dosage form to release the maximum releasable quantity of therapeutically active agent to obtain a dissolution profile of the dosage form. The data processor may be any device capable of continuously processing the data generated by the detector. In a preferred embodiment, the data processor is a computer. The data generated by the detector is preferably stored and/or analyzed by the computer. In a particularly preferred embodiment, the data collector is a computer that has data processing software. The data is preferably continuously processed by the software as it is received from the detector. In the preferred embodiment of the present invention, the detector measures the concentration of the therapeutically active agent in the media surrounding the dosage form such as in simulated gastric or intestinal fluid. By measuring the concentration of the agent in the surrounding media, the amount of agent released from the dosage form can be calculated.

The invention can also be used by removing samples from the chambers directly or from the effluent discharge of the chambers instead of, or in addition to in-line analysis. In such an embodiment the analytical methods can be any method known in the art, including but not limited to, Gas chromatography, liquid chromatography, high performance liquid chromatography (HPLC), colorimetry, uv spectroscopy, IR spectroscopy, Raman spectroscopy, near IR spectroscopy, bio-sensors, electrochemical methods, mass spectroscopy, and nuclear magnetic spectroscopy.

In the most preferred embodiment the medium analysis is performed in-line using uv spectroscopy.

It is clear to one skilled in the art that any combination of the medium analysis devices can be used as appropriate for the data required.

In another embodiment the absorption of active substance in the stomach can be simulated by not returning to the gastric chamber, all or part of the medium exiting the gastric chamber via the second outlet. The flow rate of said medium can be adjusted so that the removal rate corresponds to the in vivo gastric absorption.

The filtration cells (2 and 10) can be of any design that provides the requirements of agitation, desired volume, filtration speed, filtration efficiency, and compatibility with the active substance and the release media. The preferred filtration cells are continuous, stirred, filtration cells, such as the AMICON™ stirred ultrafiltration cell models 8003, 8010, 8050, 8200, and 8400, commercially available from Millipore Corporation. The lids and height of these cells can be modified to fulfill the requirements as described hereinabove.

The third cell (17) can be of any design that provides the requirements of agitation, desired volume, and compatibility with the active substance and the release media.

The pumps useful in the practice of the present invention can be any pump capable of attaining the desired flow rate and maintaining said flow rate constant throughout the test. These include but are not limited to, general purpose positive displacement pumps, peristaltic pumps, diaphragm pumps, HPLC quality positive displacement pumps, and centrifugal pumps. Preferred pumps useful in the invention are peristaltic pumps, diaphragm pumps, and HPLC quality positive displacement pumps. Most preferred are peristaltic pumps and HPLC quality positive displacement pumps.

Heating devices useful in the practice of the present invention can be any of those known in the art that give sufficiently uniform and accurate temperature control. The preferred heating device will be able to control the temperature to within +/−2° C. of the desired temperature. The more preferred heating device will be able to control the temperature to within +/−1° C. of the desired temperature. The most preferred heating device will be able to control the temperature in conformity with the most current recommendations in the US Pharmacopeia and like sources.

Tubing used for the content removal assembly (7) can be any tubing compatible with the release medium and the test sample. The length of said tubing is adjusted such that the lower end is below the surface of the liquid in the filtration cell (2). The cross-sectional diameter of the tubing is selected so that small particles are carried up the tubing by the flow of the release medium and so that particles do not clog the tubing. In practice, the inventors have determined that tubing with an internal diameter of 0.5 to 3.0 mm fulfills these requirements for flow rates to the cell (2) in the range 0.5 to 2.5 ml/min. For other flow rates other internal diameters may be needed. It is clear to one skilled in the art that suitable internal diameters for the said tube can be selected by trial and error, or by calculation using suitable hydrodynamic considerations.

The medium analysis sensor and controller used with the intestinal chamber can be any combination of sensor and controller that measures and permits control of physical characteristics such as, but not limited to, pH, osmolarity, conductivity, and concentration of specific ions.

The preferred medium analysis sensor and controller are any pH sensor and pH controller available in the art that permit the control of the pH in the intestinal chamber to within the target range. The most preferred medium analysis sensor and controller are any pH sensor and pH controller available in the art that has an accuracy of +/−0.02 pH units.

In the preferred embodiment the pH in the second cell (10) is controlled to the same value as that of the simulated intestinal fluid. It is clear to one skilled in the art that the pH in the said cell can be any value achievable by addition of either an acid or a base through the delivery system defined by the reservoir (23), the pump (15), and the inlet (30), and is not limited to the pH of the fluid in the reservoir (22).

The solution used to adjust the pH of the second cell can be acidic or basic. The preferred concentration of acid or base in said solution is one that requires a flow rate of said solution to be not more than 10% of the total flow of the other release media. The most preferred concentration of acid or base in said solution is one that requires a flow rate of said solution to be not more than 2% of the total flow of the other release media.

The number of cells used in the equipment can be varied depending on the information required. Three cells, as described in one embodiment above, is the preferred number when correlation with blood plasma concentration data is required. When drug absorption rate data is required it is only necessary to operate the combination of gastric and intestinal chambers. A further possibility is to add a buccal dissolution cell before the gastric chamber such that the effluent from the buccal dissolution chamber enters an inlet in the gastric chamber. Said addition can be used for either drug absorption or blood plasma concentration data.

The volumes of the three chambers and the flow rates of the various media are calculated based on the desired residence times for each of the chambers. This calculation is well known in the art and is described hereinabove.

Residence times in each of the chambers useful in the practice of this invention can be any value required to give Level A IVIVC. The preferred residence times are those that have physiological relevance. The applicant has determined by experimentation that the following ranges of residence times are useful: gastric chamber, 5-60 minutes; intestinal chamber, 1-90 minutes; circulatory chamber, greater than 30 minutes.

It is known to those skilled in the art that the safe and effective use of flow controlling devices such as pressure feed systems and pumps requires the inclusion of various other mechanical, electrical and electronic equipment. Said equipment includes, but is not limited to, pressure relief valves, check valves, pressure relief piping, pressure control systems, surge suppressors, surge tanks, de-aerators, electronic flow control systems, proportional control systems, pressure gauges, and flow gauges.

Said correlation in data is achieved by manipulation of test method variables including the number of said chambers, number of media, volume of release medium in each of said chambers, flow rate of release medium to each of said chambers, amount of the sample being tested, pH of the media, composition of the media, and temperature.

EXAMPLES

Comparative Example 1

Plunger and Basket Assembly, No Shelf Screen

The dissolution equipment was set up with the following conditions using a 20 mesh basket, as described in US20070160497(A1). Simulated Gastric Fluid (SGF) and Simulated Intestinal Fluid (SIF, pH 6.8) were prepared according to the US Pharmacopoeia 30.

| | |
|---|---|
| SGF flow to Cell 1 | 2.50 ml/min |
| SIF flow to Cell 2 | 7.35 ml/min |
| pH of Cell 2 | 6.8 |
| Cell 1 volume | 50 ml |
| Cell 2 volume | 150 ml |
| Cell 3 volume | 1600 ml |
| Temperature | 37° C. |

One half of a 200 mg ADVIL™ Advil tablet was placed in the basket. (A whole Advil tablet was too large to fit in the basket.) The plunger/basket was placed in its raised position. When conditions of temperature, and flow rates were steady and at targeted values the basket was introduced into the fluid in the first cell by pushing the plunger to its lowered. position. The tablet disintegrated in the basket, but the disintegrated solids did not leave the basket and therefore no solids transfer occurred. Based on observation, it appeared that the particle size of the disintegrated solid was too large to pass through the screen which formed the basket. Efficient solids transfer is an essential part of the test procedure, so this apparatus and method was unacceptable.

Comparative Example 2

Plunger and Coil Assembly, No Shelf Screen

Example 1 was repeated except that the basket was replaced with a coil of steel wire arranged to hold a whole 200 mg Advil tablet, and the test repeated as described. When the tablet was introduced into the fluid in the first cell the tablet disintegrated but the disintegrated solids interfered with the stirrer blade and stopped it. Efficient mixing is an essential part of the test procedure, so this apparatus and method were unacceptable.

Example 1

Plunger and Coil Assembly, Screen Shelf Positioned Above Stirrer Blade

Example 2 was repeated except that a shelf screen (20 mesh) was used in the chamber of the dissolution cell. When the tablet was introduced into the fluid it disintegrated and the disintegrated solids transferred completely to the second cell. The stirrer continued operating. This example demonstrates that the shelf screen solves the problem of solids transfer and mixing for disintegrating dosage forms.

Example 2

Sample Addition Port Covered by a Simple Cap, Screen Shelf Positioned Above Stirrer Blade In this example a shelf screen was included in the chamber of Cell 1 of a system having two cells (Cell 1 and Cell 2). Cell 1 also included a slider valve assembly which facilitated introduction of samples during continuous operation of the system.

Water was used as a surrogate for both SGF and SIF. No pH control was used. The test was set with the following conditions.

| | |
|---|---|
| Water flow to Cell 1 | 3.0 ml/min |
| Water flow to Cell 2 | 6.0 ml/min |
| Cell 1 volume | 70 ml |
| Cell 2 volume | 190 ml |

| | |
|---|---|
| Cell 3 volume | 500 ml |
| Temperature | Ambient |

With the slider valve in closed position, approx ¼ of a tablet of brilliant blue dye (Presto Dye, "Trace-a-Leak") was placed in the slider valve and the cap screwed into place. Brilliant blue dye was selected for this example to permit observation of disintegration and dissolution. When the flow rates were steady and at targeted values the slider valve was opened fully. The tablet dropped into the fluid and came to rest on the screen shelf where it disintegrated. Dissolved dye, undissolved dye, and insoluble excipients transferred completely to the second cell. The stirrer continued to operate without interruption. This example demonstrates that the slider valve/screen shelf combination permits addition of a disintegrating tablet into Cell 1 without the use of a basket and without requiring the flows to be stopped or requiring the cell to be opened.

We claim:

1. An apparatus for conducting dissolution tests comprising:
   a) a first chamber comprising a base and a shelf screen and being capable of transferring solid particles to a second chamber; wherein said shelf screen is a mesh screen compatible with said medium and having a have a mesh size of from 200 mesh to 10 mesh;
   wherein said first chamber additionally comprises tubing configured to remove liquid and particle solids from below said shelf screen to said second chamber;
   wherein said first chamber additionally comprises a lid, and said first chamber additionally comprises a hole in the lid for sample addition;
   b) said second chamber connected in series to said first chamber via said tubing and being capable of retaining solids;
   c) at least one supply of media that can be continuously passed into one or more of said chambers;
   d) a medium analysis device that analyzes effluent from said chambers for substances of interest in the tests;
   e) a heating device that controls temperature of medium in each of said chambers;
   wherein each of said chambers has a sample addition port and an agitator that mixes the sample and medium; and
   wherein said agitator of said first chamber is proximate to said base and said shelf screen is positioned in said first chamber, above said agitator, on an opposite side of said agitator from said base.

2. The apparatus according to claim 1, wherein said dosage form is a non-disintegrating dosage form wherein at least a portion of said substrate does not dissolve in said medium.

3. The apparatus according to claim 1, wherein said shelf screen has a mesh size of from 50 to 16 mesh.

4. The apparatus according to claim 1, further comprising: a third chamber connected in series to said second chamber.

5. The apparatus according to claim 4, further comprising: at least one supply of media that can be continuously passed into said third chamber; stirrer in said third chamber; medium analysis device that analyzes effluent from said third chamber for substances of interest.

6. The apparatus according to claim 1, wherein said heating device controls temperature to within +/−2° C. of a desired temperature.

7. The apparatus according to claim 6, wherein said desired temperature is 37° C.

* * * * *